US008512721B2

United States Patent
Keilman et al.

(10) Patent No.: US 8,512,721 B2
(45) Date of Patent: Aug. 20, 2013

(54) WATER RESISTANT SUNSCREEN AND INSECT REPELLANT TOWEL

(75) Inventors: Peter E. Keilman, Kansas City, MO (US); Paul M. Taylor, Overland Park, MO (US); Khue Vue, Olathe, KS (US); Christopher J. Plotz, Olathe, KS (US)

(73) Assignee: Illinois Tool Works Inc., Glenview, IL (US)

( * ) Notice: Subject to any disclaimer, the term of this patent is extended or adjusted under 35 U.S.C. 154(b) by 1063 days.

(21) Appl. No.: 10/993,338

(22) Filed: Nov. 19, 2004

(65) Prior Publication Data

US 2006/0110419 A1    May 25, 2006

(51) Int. Cl.
*A61K 8/00* (2006.01)
(52) U.S. Cl.
USPC .............. 424/403; 424/405; 424/400; 424/59
(58) Field of Classification Search
USPC .................................. 424/400, 403, 405, 59
See application file for complete search history.

(56) References Cited

U.S. PATENT DOCUMENTS

| | | | |
|---|---|---|---|
| 4,758,467 A | | 7/1988 | Lempriere |
| 5,017,365 A | | 5/1991 | Niedbala |
| 5,204,090 A | * | 4/1993 | Han ............................ 424/59 |
| 5,518,712 A | * | 5/1996 | Stewart ........................ 424/59 |
| 6,159,452 A | | 12/2000 | Stewart |
| 6,250,829 B1 | * | 6/2001 | Brower et al. .................... 401/7 |
| 2001/0055609 A1 | * | 12/2001 | Shantz et al. ................. 424/443 |
| 2002/0155281 A1 | * | 10/2002 | Lang et al. .................... 428/337 |
| 2004/0028709 A1 | * | 2/2004 | Dueva et al. .................. 424/401 |

FOREIGN PATENT DOCUMENTS

| | | |
|---|---|---|
| GB | 2 345 636 | 7/2000 |
| GB | 2345636 | 7/2000 |
| WO | WO 9400104 A1 * | 1/1994 |
| WO | 9742933 | 5/1997 |
| WO | WO 97/42933 | 11/1997 |
| WO | 0234224 | 5/2002 |
| WO | WO 02/34224 | 5/2002 |

OTHER PUBLICATIONS

WorldWise, http://web.archive.org/web/20010714190118/http://worldwise.com/biodegradable.html, 2001.*

* cited by examiner

*Primary Examiner* — Abigail Fisher
(74) *Attorney, Agent, or Firm* — Levenfeld Pearlstein, LLC

(57) ABSTRACT

A single-use disposable applicator for applying sunscreen and insect repellent to the skin is a non-woven, woven or porous fibrous material wipe that is saturated with a composition containing a waterproof sunscreen agent and an insect repellent. A film forming agent and solvent may also be present. When rubbed over the skin, the wipe provides a thin, non-greasy film that provides protection against UV absorption and insect repellent properties. The sunscreen and insect repellent combination contained in the wipe has an SPF factor between 2 and 50 and is long lasting and water resistant, which makes it ideal for use during hot or humid weather conditions.

8 Claims, No Drawings

WATER RESISTANT SUNSCREEN AND INSECT REPELLANT TOWEL

BACKGROUND OF THE INVENTION

The present invention relates to a water resistant sunscreen and insect repellent on a disposable applicator. More particularly, the present invention relates to a single-use disposable towel or wipe made from a non-woven, woven or porous material saturated with a combination water resistant sunscreen and insect repellent composition. The water resistant sunscreen and insect repellant composition, when rubbed over the skin, provides a thin, non-greasy film that provides protection against insect bites as well as the harmful effects of the sun.

It is well known that sunlight contains ultraviolet A and ultraviolet B rays (UVA and UVB rays). Prolonged exposure to the sun's ultraviolet rays can be extremely harmful to unprotected skin, and in some cases can lead to a person developing early wrinkles, skin cancer and other skin related problems. Sunscreens and sunblocks have been developed to reduce the harmful effects of the sun on the skin—they are generally contained in lotions which vary on a scale of increasing protection from 1 to 50 (although there are questions regarding the effectiveness of products claiming protection factors above about 30). The scale is called the Sun Protection Factor ("SPF"). The SPF value of a sunscreen allows the consumer to determine the degree of sunburn protection that the user desires for a given period of time from direct exposure to the sun's ultraviolet rays.

Another well known problem that arises from spending time outdoors is exposure to insects and insect bites. Mosquitoes, flies and ticks can be annoying and can cause painful bites which have the potential to spawn secondary infections or transmit diseases such as West Nile virus, Lyme disease, spotted fever and numerous other serious illnesses. Insect repellents are often used to discourage biting insects from landing on treated skin or clothing.

Combination sunscreen-insect repellents are well known compositions for protecting the skin against both insect bites and the harmful effects of prolonged exposure to the sun. Generally, they are commercially available in the form of aerosols, pump sprays or lotions that have a limited effectiveness and other considerable draw-backs. Primarily, combination sunscreen and repellant compositions can be greasy, have a foul odor and are only effective for short periods of time. These compositions typically require multiple applications and are easily removed in water. This is a distinctive problem in warm or humid climates or when a person is engaged in an activity which causes them to perspire.

In addition, aerosols, pump sprays and lotions can be somewhat difficult to apply. They are not easily controlled, especially around irregular surfaces such as the face. This can result in the unintentional inhalation of mist or vapors, or possibly cause excess chemical to come in contact and irritate the user's eyes. Furthermore, because of the high viscosity, lotions are sometimes ineffective in permitting the sunscreen-repellent composition from absorbing into skin surfaces that are partially covered by hair, such as the legs or chest. Lotion, even after being massaged into such areas after application, tends to intermingle with the hair. Instead of being absorbed into the skin, the lotion will merely congeal on top of the surface—providing less protection for the user.

Furthermore, existing aerosols, pump sprays and lotions containing both sunscreen and insect repellent agents are inconvenient and bulky. They are relatively heavy and require a large storage area for transporting. In addition, the applicators, e.g., pump and spray bottles often break before the compositions are used up, thus wasting product.

Accordingly, there exists a need for a combination sunscreen and insect repellent that is long lasting and effective, but fast, easy and safe to apply. Desirably, such a combination sunscreen and insect repellant provides a single use, one-step controlled application that is water resistant, non-greasy, pleasant smelling and cost effective. More desirably, such a composition has reasonable manufacturing and packaging costs, and uses industry standard effective and long lasting materials.

BRIEF SUMMARY OF THE INVENTION

A disposable personal applicator is formed from a non-woven, woven or porous fibrous material that is saturated with a composition containing a waterproof sunscreen and insect repellent. A preferred composition includes a sunscreen agent, an insect repellent agent, a solvent and a film forming agent present in an amount effective to form a thin film when the composition is applied to the skin of a person.

The sunscreen agent is present in an amount effective to provide a SPF from about 5 to 50. Preferably, the sunscreen agent is present in an amount effective to provide a SPF from about 15 to 30.

One suitable sunscreen agent is a composition of homosalate at a concentration of about 2.0 percent to about 15.0 percent by weight of the total composition, octinoxate at a concentration of about 7.5 percent by weight of the total composition, octisalate at a concentration of about 4.0 percent to about 5.0 percent by weight of the total composition and oxybenzone at a concentration of about 5.0 percent to about 6.0 percent by weight of the total composition. The sunscreen can include inactive ingredients, such as acrylates, octylacrylamide copolymer or an alcohol such as ethanol.

A preferred insect repellent agent is DEET present in a concentration of about 5.0 to about 35.0 weight percent of the weight percent of the total composition. A suitable delivery agent is an alcohol based agent, such as ethanol.

The applicator towel is a non-woven, woven or porous fibrous material. The material can be a polymeric fiber, a natural fiber, or a blend of polymeric and natural fibers. Suitable polymeric non-woven, woven or porous fibers are polyethylene fibers, polypropylene fibers or a blend thereof. The non-woven, woven or porous fibrous material can also be formed as a biodegradable material.

These and other features and advantages of the present invention will be apparent from the following detailed description, in conjunction with the appended claims.

DETAILED DESCRIPTION OF THE INVENTION

While the present invention is susceptible of embodiment in various forms, there is hereinafter described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

The present invention provides a single use disposable personal applicator is formed as a towel or wipe made of a non-woven, woven or porous fibrous material that is saturated with a composition containing a waterproof sunscreen and insect repellent. When rubbed over a user's skin, the towel releases a thin, non-greasy film containing the combination sunscreen-repellent composition that provides the wearer with protection against insect bites as well as the harmful effects of prolonged exposure to the sun.

A preferred form of the sunscreen-repellent composition contains a sun a sunscreen agent, an insect repellent agent, a solvent and a film forming agent which is present in an amount effective to form a thin film when the composition is applied to the skin of a user. The composition is saturated in a wipe, preferably a non-woven, woven or porous wipe, which is used to apply the composition to the skin. Once the wipe is rubbed over the skin, sunscreen-repellent composition is released from the wipe and absorbed into the surface of the skin.

It is anticipated that a variety of sunscreen active agents can be used in the present towel composition. For example, sunscreen active agents such as aminobenzoic acid up to about 15.0 percent by weight, avobenzone up to about 3.0 percent by weight, cinoxate up to about 3.0 percent by weight, dioxybenzone up to about 3.0 percent by weight, methyl anthranilate up to about 5.0 percent by weight, octocrylene up to about 10.0 percent by weight, pandimate O up to about 8.0 percent by weight, phenyl benzimidazone sulfonic acid up to about 4.0 percent by weight, sulisobenzone up to about 10.0 percent by weight, titanium dioxide up to about 25.0 percent by weight, trolamine salicylate up to about 12.0 percent by weight and zinc oxide up to about 25.0 percent by weight are anticipated to be suitable for the present towel composition.

A present applicator is a towel article having a sunscreen active agent composition of homosalate at a concentration of about 2.0 percent to about 15.0 percent by weight, octinoxate at a concentration of about 7.5 percent by weight, octisalate at a concentration of about 4.0 percent to about 5.0 percent by weight and oxybenzone at a concentration of about 5.0 percent to about 6.0 percent by weight. The inactive ingredients in the sunscreen can include, for example, acrylates, octylacrylamide copolymer, alcohol (such as ethanol) and, if desired, a fragrance.

The resulting sunscreen has a long efficacy period when subjected to perspiration, underwater submersion or extreme environmental conditions having high humidity. Moreover, the sunscreen agent is present in the composition in an amount effective to provide a SPF of between about 5 and 50, and preferably about 15 to 30.

A suitable insect repellent is M-toluamide, N,N-diethyl, commonly known as DEET, in an amount of about 2.0 percent to about 99.0 percent, and preferably, about 5.0 weight percent to about 35.0 weight percent. DEET is known in the art and is the active ingredient in many commercially available insect repellent products. It has been shown to be safe for direct application to human skin, and is effective in repelling biting insects such as mosquitoes, flies and ticks which may carry infectious diseases. The resulting composition containing the repellent agent has a pleasant odor, and is applied in such a manner that minimizes concerns regarding inhaling or ingesting mists or vapors. Since the DEET is combined with the sunscreen agent, the repellent agent is highly resistant to water, yet can be easily removed by scrubbing with soap and water. The composition was tested under strict laboratory conditions using appropriate protocols approved by the FDA and EPA.

One solvent for use in the present formulation of the water resistant sunscreen and insect repellent composition is an alcohol such as ethanol. The solvent is present in a concentration of about 2.0 to about 80.0 percent by weight of the composition, and preferably is present in a concentration of about 60.0 percent of the composition. Suitable film forming agents are DEET and sunscreen mixtures. The film forming agent serves to protect, and is present in a concentration of about 2.0 to about 80.0 percent by weight of the composition, and preferably is present in a concentration of about 40.0 percent of the composition.

The towel or wipe applicator of the present invention is a non-woven, woven or porous fibrous material which has a high wet strength and provides a pleasant feel when rubbed over the skin. It is sufficiently bulky and strong to prevent break up during use, but not too substantive to make the user reluctant to dispose of the article after single use. The fibrous material can be made from either a natural or polymeric fiber, and has a basis weight of about 15 to 90 grams per square meter (gsm). Suitable polymeric materials for forming the fibers of the non-woven, woven or porous towel or wipe are polyethylene and polypropylene. It is anticipated that other synthetic materials and natural materials having similar characteristics and weight would be equally suitable for use in the current invention, which other synthetic and natural materials are within the scope and spirit of the present invention. It is also anticipated that a readily biodegradable or dispersible material can be used for the towel to reduce environmental concerns regarding disposal or the like.

The towel or wipe applicator is evenly saturated with the sunscreen-repellent composition in such a manner that the composition is released when the wipe is rubbed over the user's skin. One embodiment of the towel has the wiper (dry towel) saturated with a composition of about 1.0 to about 45.0 percent by weight of sunscreen, about 1.0 to about 45.0 percent by weight of insect repellent, about 2.0 to about 80.0 percent by weight of solvent and about 1.0 to about 80.0 percent by weight of film forming agent. A preferred towel includes the sunscreen agent mixtures in a concentration of about 38.0 percent, the alcohol solvent (e.g., ethanol) in a concentration of about 47.0 percent, and the film forming agent DEET and sunscreen mixtures in a concentration of about 31.0 percent. A present applicator includes a towel that is about 22.4 percent by weight of the applicator in total (total towel and composition), DEET that is about 15.5 percent by weight of the applicator in total; sunscreen that is about 15.5 percent by weight of the applicator in total and alcohol (e.g., ethanol) that is about 46.5 percent by weight of the applicator in total.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments disclosed is intended or should be inferred. The disclosure is intended to cover by the appended claims all such modifications as fall within the scope of the claims.

What is claimed is:

1. A disposable personal applicator towel comprising:
   a biodegradable fibrous material saturated with a composition of a waterproof sunscreen agent, an insect repellent, and a solvent,
   the sunscreen agent and the insect repellant forming a film forming agent present in an amount effective to form a thin film when the composition is applied to a skin of a person, the film forming agent present in a concentration of 40 percent by weight of the total composition, wherein the sunscreen agent is a composition of homosalate at a concentration of about 2.0 percent to about 15.0 percent by weight of the total composition, octinoxate at a concentration of about 7.5 percent by weight of the total composition, octisalate at a concentration of about 4.0 percent to about 5.0 percent by weight of the total composition and oxybenzone at a concentration of about 5.0 percent to about 6.0 percent by weight of the total composition, the sunscreen agent being present in an amount effective to provide a SPF from about 5 to 50, wherein the insect repellent agent is DEET present in a concentration of about 5.0 to about 35.0 weight percent of the weight percent of the total composition, and wherein the solvent is ethanol having a concentration of 60.0 percent by weight of the total composition.

2. The applicator towel in accordance with claim 1, wherein the sunscreen agent is present in an amount effective to provide a SPF from about 15 to 30.

3. The applicator towel in accordance with claim 1 wherein the fibrous material is a non-woven material, a woven material or a porous material.

4. The applicator towel in accordance with claim 3 wherein the fibrous material is a non-woven material.

5. The applicator towel in accordance with claim 4, wherein the non-woven fibrous material is a polymeric fiber, a natural fiber, or a blend of natural and polymeric fibers.

6. The applicator towel in accordance with claim 4, wherein the non-woven fibrous material is a polymeric fiber and the polymeric non-woven fibrous material is formed from polyethylene fibers.

7. The applicator towel in accordance with claim 4, wherein the non-woven fibrous material is a polymeric fiber and the polymeric non-woven fibrous material is formed from polypropylene fibers.

8. The applicator towel in accordance with claim 4, wherein the non-woven fibrous material is a polymeric fiber and the polymeric non-woven fibrous material is formed from a blend of polyethylene and polypropylene fibers.

\* \* \* \* \*

UNITED STATES PATENT AND TRADEMARK OFFICE
CERTIFICATE OF CORRECTION

PATENT NO. : 8,512,721 B2
APPLICATION NO. : 10/993338
DATED : August 20, 2013
INVENTOR(S) : Peter E. Keilman et al.

It is certified that error appears in the above-identified patent and that said Letters Patent is hereby corrected as shown below:

In the Claims

In claim 1, Line 16, the phrase "weight percent of the weight percent of the total composition" should read "weight percent of the total composition".

Signed and Sealed this
Third Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,512,721 B2 | Page 1 of 1 |
| APPLICATION NO. | : 10/993338 | |
| DATED | : August 20, 2013 | |
| INVENTOR(S) | : Peter E. Keilman et al. | |

It is certified that error appears in the above-identified patent and that said Letters Patent is hereby corrected as shown below:

In the Claims

Col. 5, lines 14-15, in claim 1, the phrase "weight percent of the weight percent of the total composition" should read "weight percent of the total composition".

This certificate supersedes the Certificate of Correction issued December 3, 2013.

Signed and Sealed this
Fourth Day of February, 2014

Michelle K. Lee
*Deputy Director of the United States Patent and Trademark Office*